(12) United States Patent
Bancroft et al.

(10) Patent No.: US 11,426,498 B2
(45) Date of Patent: Aug. 30, 2022

(54) SYSTEMS AND METHODS FOR MANAGING BLOOD DONATIONS

(71) Applicant: APPLIED SCIENCE, INC., Grass Valley, CA (US)

(72) Inventors: James A. Bancroft, Grass Valley, CA (US); James E. Goodnow, II, Grass Valley, CA (US)

(73) Assignee: Applied Science, Inc., Grass Valley, CA (US)

( * ) Notice: Subject to any disclaimer, the term of this patent is extended or adjusted under 35 U.S.C. 154(b) by 1075 days.

(21) Appl. No.: 14/727,745

(22) Filed: Jun. 1, 2015

(65) Prior Publication Data
US 2015/0343123 A1    Dec. 3, 2015

Related U.S. Application Data

(60) Provisional application No. 62/005,673, filed on May 30, 2014.

(51) Int. Cl.
*A61M 1/02* (2006.01)
*A61B 5/15* (2006.01)
(Continued)

(52) U.S. Cl.
CPC ......... *A61M 1/024* (2013.01); *A61B 5/15003* (2013.01); *A61B 5/150809* (2013.01);
(Continued)

(58) Field of Classification Search
CPC .. A61M 1/024; A61M 39/22; A61M 2205/11; A61M 2205/581;
(Continued)

(56) References Cited

U.S. PATENT DOCUMENTS

| 4,083,363 A | * | 4/1978 | Philpot, Jr. | ........ | A61B 5/02035 |
| | | | | | 600/370 |
| 4,377,852 A | | 3/1983 | Thompson | | |

(Continued)

FOREIGN PATENT DOCUMENTS

| CN | 1348740 A | 5/2002 |
| CN | 1503954 A | 6/2004 |

(Continued)

OTHER PUBLICATIONS

WHO Guidelines for drawing blood, May 19, 2010. http://www.who.int/injection_safety/phleb_final_screen_ready.pdf.*

(Continued)

*Primary Examiner* — Alex M Valvis
*Assistant Examiner* — Yasmeen S Warsi
(74) *Attorney, Agent, or Firm* — Shay Glenn LLP

(57) ABSTRACT

Apparatuses and methods of using them to collect blood, are provided, by first ensuring that the patient's skin is properly cleaned, to prevent contamination of the collected blood. One feature is a blood collection device configured to collect blood from a patient. Another feature is a scrub timer integrated into the device and configured to indicate to a user a scrub time period prior to beginning a blood draw process. The scrub timer can be configured to audibly and/or visually indicate to a user the start and stop times of a scrub cleaning process. In one embodiment, the scrub timer can be restarted, either manually or automatically, if the scrub cleaning process is not followed properly.

27 Claims, 2 Drawing Sheets

(51) Int. Cl.
  *A61M 39/22* (2006.01)
  *A61B 5/155* (2006.01)
  *A61J 1/10* (2006.01)
  *A61J 1/16* (2006.01)

(52) U.S. Cl.
  CPC ............ *A61M 39/22* (2013.01); *A61B 5/155* (2013.01); *A61B 5/150328* (2013.01); *A61J 1/10* (2013.01); *A61J 1/16* (2013.01); *A61M 2205/11* (2013.01); *A61M 2205/581* (2013.01); *A61M 2205/583* (2013.01)

(58) Field of Classification Search
  CPC ..... A61M 2205/583; A61B 19/26; A61J 1/10; A61J 1/16
  See application file for complete search history.

(56) References Cited

U.S. PATENT DOCUMENTS

| | | |
|---|---|---|
| 4,451,158 A * | 5/1984 | Selwyn ............... G04G 13/00 368/107 |
| RE33,924 E | 5/1992 | Valeri |
| 5,403,279 A | 4/1995 | Inaba et al. |
| 5,403,304 A | 4/1995 | Ishida |
| 5,611,048 A | 3/1997 | Jacobs et al. |
| 5,658,240 A | 8/1997 | Urdahl et al. |
| 5,666,500 A | 9/1997 | Roberson |
| 5,845,289 A | 12/1998 | Baumeister et al. |
| 5,857,194 A | 1/1999 | Kelliher et al. |
| 5,912,669 A | 6/1999 | Hsia |
| 5,973,665 A | 10/1999 | Davie et al. |
| 6,008,811 A | 12/1999 | McMillan |
| 6,014,702 A | 1/2000 | King et al. |
| 6,026,684 A | 2/2000 | Calder |
| 6,049,832 A | 4/2000 | Brim et al. |
| 6,113,554 A | 9/2000 | Gilcher et al. |
| 6,131,510 A | 10/2000 | Gasquez |
| 6,216,164 B1 | 4/2001 | Zaremba |
| 6,233,525 B1 | 5/2001 | Langley et al. |
| 6,252,591 B1 | 6/2001 | Dockweiler et al. |
| 6,256,643 B1 | 7/2001 | Cork et al. |
| 6,259,447 B1 | 7/2001 | Kanetake et al. |
| 6,289,382 B1 | 9/2001 | Bowman Amuah |
| 6,327,624 B1 | 12/2001 | Mathewson et al. |
| 6,332,163 B1 | 12/2001 | Bowman Amuah |
| 6,334,144 B1 | 12/2001 | Horwitz |
| 6,339,832 B1 | 1/2002 | Bowman Amuah |
| 6,342,905 B1 | 1/2002 | Diedrich et al. |
| 6,366,658 B1 | 4/2002 | Bjornberg et al. |
| 6,381,654 B1 | 4/2002 | Brawn et al. |
| 6,402,702 B1 | 6/2002 | Gilcher et al. |
| 6,405,924 B1 | 6/2002 | Shah |
| 6,406,919 B1 | 6/2002 | Tyrrell |
| 6,434,568 B1 | 8/2002 | Bowman Amuah |
| 6,434,628 B1 | 8/2002 | Bowman Amuah |
| 6,438,594 B1 | 8/2002 | Bowman Amuah |
| 6,442,748 B1 | 8/2002 | Bowman Amuah |
| 6,446,110 B1 | 9/2002 | Lection et al. |
| 6,453,356 B1 | 9/2002 | Sheard et al. |
| 6,477,580 B1 | 11/2002 | Bowman Amuah |
| 6,477,665 B1 | 11/2002 | Bowman Amuah |
| 6,480,895 B1 | 11/2002 | Gray et al. |
| 6,496,850 B1 | 12/2002 | Bowman Amuah |
| 6,502,213 B1 | 12/2002 | Bowman Amuah |
| 6,508,778 B1 | 1/2003 | Verkaart et al. |
| 6,511,439 B1 | 1/2003 | Tabata et al. |
| 6,519,605 B1 | 2/2003 | Gilgen et al. |
| 6,529,909 B1 | 3/2003 | Bowman Amuah |
| 6,529,948 B1 | 3/2003 | Bowman Amuah |
| 6,539,396 B1 | 3/2003 | Bowman Amuah |
| 6,549,949 B1 | 4/2003 | Bowman Amuah |
| 6,550,057 B1 | 4/2003 | Bowman Amuah |
| 6,571,282 B1 | 5/2003 | Bowman Amuah |
| 6,578,068 B1 | 6/2003 | Bowman Amuah |
| 6,582,386 B2 | 6/2003 | Min et al. |
| 6,601,192 B1 | 7/2003 | Bowman Amuah |
| 6,601,234 B1 | 7/2003 | Bowman Amuah |
| 6,606,660 B1 | 8/2003 | Bowman Amuah |
| 6,611,806 B1 | 8/2003 | Harvey |
| 6,615,199 B1 | 9/2003 | Bowman Amuah |
| 6,615,253 B1 | 9/2003 | Bowman Amuah |
| 6,622,176 B2 | 9/2003 | Jones et al. |
| 6,636,242 B2 | 10/2003 | Bowman Amuah |
| 6,640,238 B1 | 10/2003 | Bowman Amuah |
| 6,640,244 B1 | 10/2003 | Bowman Amuah |
| 6,640,249 B1 | 10/2003 | Bowman Amuah |
| 6,641,552 B1 | 11/2003 | Kingsley et al. |
| 6,665,868 B1 | 12/2003 | Knowles et al. |
| 6,673,314 B1 | 1/2004 | Burbank et al. |
| 6,714,945 B1 | 3/2004 | Foote et al. |
| 6,715,145 B1 | 3/2004 | Bowman Amuah |
| 6,718,334 B1 | 4/2004 | Han |
| 6,730,054 B2 | 5/2004 | Pierce et al. |
| 6,742,015 B1 | 5/2004 | Bowman Amuah |
| 6,773,413 B2 | 8/2004 | Keller et al. |
| 6,808,503 B2 | 10/2004 | Farrell et al. |
| 6,816,880 B1 | 11/2004 | Strandberg et al. |
| 6,842,906 B1 | 1/2005 | Bowman Amuah |
| 6,862,573 B2 | 3/2005 | Kendall et al. |
| 6,884,228 B2 | 4/2005 | Brown et al. |
| 6,934,848 B1 | 8/2005 | King et al. |
| 6,944,596 B1 | 9/2005 | Gray et al. |
| 6,949,079 B1 | 9/2005 | Westberg et al. |
| 6,976,164 B1 | 12/2005 | King et al. |
| 6,980,989 B2 | 12/2005 | Silverman et al. |
| 6,994,790 B2 | 2/2006 | Corbin et al. |
| 6,996,542 B1 | 2/2006 | Landry |
| 7,072,769 B2 | 7/2006 | Fletcher Haynes et al. |
| 7,076,032 B1 | 7/2006 | Pirasteh et al. |
| 7,087,047 B2 | 8/2006 | Kraus et al. |
| 7,169,352 B1 | 1/2007 | Felt et al. |
| 7,219,094 B2 | 5/2007 | Schiel et al. |
| 7,269,844 B2 | 9/2007 | Elteto et al. |
| 7,289,964 B1 | 10/2007 | Bowman Amuah |
| 7,334,015 B1 | 2/2008 | Phillips |
| 7,354,415 B2 | 4/2008 | Bainbridge et al. |
| 7,373,373 B2 | 5/2008 | McElhannon |
| 7,380,024 B2 | 5/2008 | Peterson et al. |
| 7,415,438 B1 | 8/2008 | Berman et al. |
| 7,421,427 B2 | 9/2008 | DeForeest et al. |
| 7,430,478 B2 | 9/2008 | Fletcher-Haynes et al. |
| 7,434,166 B2 | 10/2008 | Acharya et al. |
| 7,454,399 B2 | 11/2008 | Matichuk |
| 7,475,143 B2 | 1/2009 | Hartmann et al. |
| 7,479,123 B2 | 1/2009 | Briggs |
| 7,540,021 B2 | 5/2009 | Page |
| 7,558,777 B1 | 7/2009 | Santos |
| 7,566,315 B2 | 7/2009 | Hirabuki |
| 7,574,376 B1 | 8/2009 | Berman et al. |
| 7,597,250 B2 | 10/2009 | Finn |
| 7,704,454 B1 | 4/2010 | Langley et al. |
| 7,708,710 B2 | 5/2010 | Min et al. |
| 7,739,227 B2 | 6/2010 | Jordan et al. |
| 7,752,178 B2 | 7/2010 | Anderson |
| 7,754,149 B2 | 7/2010 | Sugiyama |
| 7,844,472 B1 | 11/2010 | Akin et al. |
| 7,844,521 B1 | 11/2010 | Hoag et al. |
| 7,850,634 B2 | 12/2010 | Briggs |
| 7,860,726 B2 | 12/2010 | Connely et al. |
| 7,877,402 B1 | 1/2011 | Weiss et al. |
| 7,900,298 B1 | 3/2011 | Char et al. |
| 7,937,583 B2 | 5/2011 | Thornton et al. |
| 7,949,546 B1 | 5/2011 | Klieman et al. |
| 7,962,899 B2 | 6/2011 | McCullough et al. |
| 7,992,203 B2 | 8/2011 | Relyea |
| 8,036,987 B1 | 10/2011 | Grbac et al. |
| 8,060,382 B1 | 11/2011 | Lee et al. |
| 8,060,423 B1 | 11/2011 | Rukonic et al. |
| 8,060,500 B1 | 11/2011 | Fitch et al. |
| 8,086,730 B2 | 12/2011 | Ribak et al. |
| 8,108,227 B1 | 1/2012 | Rogers et al. |
| 8,108,271 B1 | 1/2012 | Duncan et al. |
| 8,146,000 B1 | 3/2012 | Boliek et al. |

(56) References Cited

U.S. PATENT DOCUMENTS

| | | |
|---|---|---|
| 8,155,950 B1 | 4/2012 | Bickerstaff |
| 8,166,473 B2 | 4/2012 | Kinsey et al. |
| 8,170,958 B1 | 5/2012 | Gremett et al. |
| 8,185,426 B1 | 5/2012 | Khoubyari |
| 8,196,061 B1 | 6/2012 | Bhojan |
| 8,204,805 B2 | 6/2012 | Eftekhari et al. |
| 8,209,229 B1 | 6/2012 | Weiss et al. |
| 8,214,276 B1 | 7/2012 | Preece et al. |
| 8,219,504 B1 | 7/2012 | Weiss et al. |
| 8,280,787 B1 | 10/2012 | Gandhi |
| 8,285,622 B1 | 10/2012 | Rao et al. |
| 8,286,199 B1 | 10/2012 | Pulaski et al. |
| 8,291,047 B2 | 10/2012 | Liu et al. |
| 8,296,206 B1 | 10/2012 | Del Favero et al. |
| 8,306,255 B1 | 11/2012 | Degnan |
| 8,321,309 B1 | 11/2012 | Jain et al. |
| 8,326,725 B2 | 12/2012 | Elwell et al. |
| 8,335,728 B1 | 12/2012 | Dahodwala et al. |
| 8,346,753 B2 | 1/2013 | Hayes |
| 8,346,929 B1 | 1/2013 | Lai |
| 8,352,350 B1 | 1/2013 | Del Favero et al. |
| 8,364,522 B1 | 1/2013 | Gevelber |
| 8,375,324 B1 | 2/2013 | Zubizarreta et al. |
| 8,380,590 B1 | 2/2013 | Rukonic et al. |
| 8,407,113 B1 | 3/2013 | Eftekhari et al. |
| 8,452,748 B1 | 5/2013 | Pugh |
| 8,463,622 B2 | 6/2013 | Garms et al. |
| 8,468,130 B2 | 6/2013 | Bhandari et al. |
| 8,473,263 B2 | 6/2013 | Tolone et al. |
| 8,473,858 B2 | 6/2013 | Buchanan et al. |
| 8,484,626 B2 | 7/2013 | Nagulu et al. |
| 8,495,596 B1 | 7/2013 | Safavi-Naini |
| 8,521,628 B1 | 8/2013 | Gowen et al. |
| 8,527,291 B1 | 9/2013 | Kochendorfer |
| 8,543,932 B2 | 9/2013 | Fields et al. |
| 8,566,313 B1 | 10/2013 | Zubizarreta et al. |
| 8,568,356 B2 | 10/2013 | Lebel et al. |
| 8,571,885 B2 | 10/2013 | Andros et al. |
| 8,600,835 B1 | 12/2013 | Lueck |
| 8,640,105 B2 | 1/2014 | Yaffe |
| 8,649,770 B1 | 2/2014 | Cope et al. |
| 8,655,726 B1 | 2/2014 | Favero et al. |
| 8,660,945 B1 | 2/2014 | Pariante et al. |
| 8,668,138 B1 | 3/2014 | Schwarz et al. |
| 8,688,504 B2 | 4/2014 | Reisman |
| 8,689,016 B2 | 4/2014 | Morten et al. |
| 8,707,409 B2 | 4/2014 | Shah et al. |
| 8,713,005 B2 | 4/2014 | Benson |
| 8,744,197 B2 | 6/2014 | Fertik et al. |
| 8,744,923 B1 | 6/2014 | McKay et al. |
| 8,751,292 B2 | 6/2014 | Del Favero et al. |
| 8,752,170 B1 | 6/2014 | Newstadt et al. |
| 8,768,833 B2 | 7/2014 | Freishtat et al. |
| 8,775,070 B1 | 7/2014 | Bhatia |
| 8,793,777 B2 | 7/2014 | Colson |
| 8,798,596 B2 | 8/2014 | Shuster et al. |
| 8,826,145 B1 | 9/2014 | Kirkpatrick et al. |
| 2002/0013523 A1 | 1/2002 | Csore et al. |
| 2002/0087356 A1 | 7/2002 | Andros et al. |
| 2002/0116219 A1 | 8/2002 | Ibok et al. |
| 2003/0004751 A1 | 1/2003 | Ng et al. |
| 2003/0032868 A1 | 2/2003 | Graskov et al. |
| 2003/0037023 A1 | 2/2003 | Lyakovetsky et al. |
| 2003/0040835 A1 | 2/2003 | Ng et al. |
| 2003/0069480 A1 | 4/2003 | Ng et al. |
| 2003/0120593 A1 | 6/2003 | Bansal et al. |
| 2003/0154108 A1 | 8/2003 | Fletcher Haynes et al. |
| 2003/0002002 A1 | 10/2003 | Wells et al. |
| 2003/0229846 A1 | 12/2003 | Sethi et al. |
| 2004/0046787 A1 | 3/2004 | Henry et al. |
| 2004/0103040 A1 | 5/2004 | Ronaghi et al. |
| 2004/0117376 A1 | 6/2004 | Lavin et al. |
| 2004/0153432 A1 | 8/2004 | O'Halloran et al. |
| 2004/0171983 A1 | 9/2004 | Sparks et al. |
| 2004/0193613 A1 | 9/2004 | Armand |
| 2004/0214148 A1 | 10/2004 | Salvino et al. |
| 2004/0230216 A1 | 11/2004 | LeVaughn et al. |
| 2004/0267562 A1 | 12/2004 | Fuhrer et al. |
| 2005/0038675 A1 | 2/2005 | Siekman et al. |
| 2005/0071193 A1 | 3/2005 | Kalies |
| 2005/0096973 A1 | 5/2005 | Heyse et al. |
| 2005/0137908 A1 | 6/2005 | Fusari et al. |
| 2005/0182726 A1 | 8/2005 | Honeycutt et al. |
| 2005/0204900 A1 | 9/2005 | Burton |
| 2005/0234964 A1 | 10/2005 | Batra et al. |
| 2005/0240437 A1 | 10/2005 | Cunningham |
| 2005/0243655 A1 | 11/2005 | McCutcheon et al. |
| 2005/0278261 A1 | 12/2005 | Omanson et al. |
| 2006/0026067 A1 | 2/2006 | Nicholas et al. |
| 2006/0026519 A1 | 2/2006 | Vaindiner et al. |
| 2006/0075224 A1 | 4/2006 | Tao |
| 2006/0085478 A1 | 4/2006 | Landau et al. |
| 2006/0111943 A1 | 5/2006 | Wu |
| 2006/0190566 A1 | 8/2006 | Roach |
| 2006/0247971 A1 | 11/2006 | Dresden et al. |
| 2007/0055483 A1 | 3/2007 | Lee et al. |
| 2007/0106647 A1 | 5/2007 | Schwalb |
| 2007/0112574 A1 | 5/2007 | Greene |
| 2007/0130111 A1 | 6/2007 | Stoudt et al. |
| 2007/0143660 A1 | 6/2007 | Huey et al. |
| 2007/0198744 A1 | 8/2007 | Wensley et al. |
| 2007/0219826 A1 | 9/2007 | Brodsky et al. |
| 2007/0220494 A1 | 9/2007 | Spooner |
| 2007/0250390 A1 | 10/2007 | Lee et al. |
| 2007/0276678 A1 | 11/2007 | Nichols |
| 2007/0282280 A1 | 12/2007 | Tennican |
| 2008/0064986 A1 | 3/2008 | Kraemer et al. |
| 2008/0097952 A1 | 4/2008 | Eswaran |
| 2008/0132311 A1 | 6/2008 | Walker |
| 2008/0133551 A1 | 6/2008 | Wensley et al. |
| 2008/0133736 A1 | 6/2008 | Wensley et al. |
| 2008/0148160 A1 | 6/2008 | Holmes et al. |
| 2008/0208750 A1 | 8/2008 | Chen |
| 2009/0037264 A1 | 2/2009 | Del Favero et al. |
| 2009/0037266 A1 | 2/2009 | Weiss et al. |
| 2009/0048870 A1 | 2/2009 | Godshall et al. |
| 2009/0076885 A1 | 3/2009 | Fein et al. |
| 2009/0187462 A1 | 7/2009 | Gevelber et al. |
| 2009/0191174 A1 | 7/2009 | Boudreau et al. |
| 2009/0204964 A1 | 8/2009 | Foley et al. |
| 2009/0288037 A1 | 11/2009 | Lawton et al. |
| 2010/0049542 A1 | 2/2010 | Benjamin et al. |
| 2010/0049576 A1 | 2/2010 | Wilson et al. |
| 2010/0063838 A1 | 3/2010 | Schumacher et al. |
| 2010/0083358 A1 | 4/2010 | Govindarajan et al. |
| 2010/0100424 A1 | 4/2010 | Buchanan et al. |
| 2010/0138241 A1 | 6/2010 | Ruark et al. |
| 2010/0142447 A1 | 6/2010 | Schlicht et al. |
| 2010/0168615 A1 | 7/2010 | Amano et al. |
| 2010/0205112 A1 | 8/2010 | Reynolds et al. |
| 2010/0215280 A1 | 8/2010 | Abdo et al. |
| 2010/0256974 A1 | 10/2010 | Xu et al. |
| 2010/0269049 A1 | 10/2010 | Fearon |
| 2010/0306080 A1 | 12/2010 | Trandal et al. |
| 2011/0010214 A1 | 1/2011 | Carruth |
| 2011/0022425 A1 | 1/2011 | Block et al. |
| 2011/0041153 A1 | 2/2011 | Simon et al. |
| 2011/0047230 A1 | 2/2011 | McGee |
| 2011/0106759 A1 | 5/2011 | Brown |
| 2011/0130114 A1 | 6/2011 | Boudville |
| 2011/0191254 A1 | 8/2011 | Womack |
| 2012/0010553 A1 | 1/2012 | Alqvist et al. |
| 2012/0016721 A1 | 1/2012 | Weinman |
| 2012/0022892 A1 | 1/2012 | Feldman et al. |
| 2012/0036565 A1 | 2/2012 | Gamez et al. |
| 2012/0054625 A1 | 3/2012 | Pugh et al. |
| 2012/0072232 A1 | 3/2012 | Frankham et al. |
| 2012/0096021 A1 | 4/2012 | Wiser et al. |
| 2012/0130962 A1 | 5/2012 | Wiser et al. |
| 2012/0136678 A1 | 5/2012 | Steinberg |
| 2012/0173397 A1 | 7/2012 | Elwell et al. |
| 2012/0191703 A1 | 7/2012 | Huff |
| 2012/0191716 A1 | 7/2012 | Omoigui |
| 2012/0215560 A1 | 8/2012 | Wartenfeld et al. |

(56) References Cited

U.S. PATENT DOCUMENTS

| | | |
|---|---|---|
| 2012/0218127 A1 | 8/2012 | Kroen |
| 2012/0253801 A1 | 10/2012 | Santos-Lang et al. |
| 2012/0265099 A1 | 10/2012 | Goodnow et al. |
| 2012/0329529 A1 | 12/2012 | van der Raadt |
| 2013/0030889 A1 | 1/2013 | Davich et al. |
| 2013/0061323 A1 | 3/2013 | Liske |
| 2013/0096501 A1 | 4/2013 | Arene et al. |
| 2013/0138501 A1 | 5/2013 | Litzow et al. |
| 2013/0202482 A1 | 8/2013 | Froimson |
| 2013/0204778 A1 | 8/2013 | Connors et al. |
| 2013/0290408 A1 | 10/2013 | Stephure et al. |
| 2013/0291024 A1 | 10/2013 | Lefevre et al. |
| 2013/0297349 A1 | 11/2013 | Epstein et al. |
| 2013/0304496 A1 | 11/2013 | Rangadass |
| 2013/0339858 A1 | 12/2013 | Corfield |
| 2013/0346144 A1 | 12/2013 | Ferren et al. |
| 2013/0346527 A1 | 12/2013 | Shah et al. |
| 2014/0004949 A1 | 1/2014 | Miura et al. |
| 2014/0004956 A1 | 1/2014 | Miura et al. |
| 2014/0033230 A1 | 1/2014 | Hanna et al. |
| 2014/0046678 A1 | 2/2014 | Lacy et al. |
| 2014/0052469 A1 | 2/2014 | Andros et al. |
| 2014/0052680 A1 | 2/2014 | Nitz et al. |
| 2014/0052681 A1 | 2/2014 | Nitz et al. |
| 2014/0077932 A1 | 3/2014 | Rooyakkers |
| 2014/0088998 A1 | 3/2014 | Boyer et al. |
| 2014/0095363 A1 | 4/2014 | Caldwell |
| 2014/0096226 A1 | 4/2014 | Barkan |
| 2014/0108397 A1 | 4/2014 | Zubizarreta et al. |
| 2014/0115679 A1 | 4/2014 | Barton et al. |
| 2014/0122135 A1 | 5/2014 | Bain |
| 2014/0136280 A1 | 5/2014 | Farahat et al. |
| 2014/0136541 A1 | 5/2014 | Farahat et al. |
| 2014/0143270 A1 | 5/2014 | Amulu et al. |
| 2014/0149842 A1 | 5/2014 | Murthy et al. |
| 2014/0156345 A1 | 6/2014 | Eskey et al. |
| 2014/0164484 A1 | 6/2014 | Vonog et al. |
| 2014/0172625 A1 | 6/2014 | Reisman |
| 2014/0172751 A1 | 6/2014 | Greenwood |
| 2014/0180802 A1 | 6/2014 | Boal |
| 2014/0188649 A1 | 7/2014 | Messinger et al. |
| 2014/0189048 A1 | 7/2014 | Messinger et al. |
| 2014/0189851 A1 | 7/2014 | Domke et al. |
| 2014/0189876 A1 | 7/2014 | Messinger et al. |
| 2014/0207521 A1 | 7/2014 | Onder et al. |
| 2014/0207601 A1 | 7/2014 | Soorianarayanan et al. |
| 2014/0207862 A1 | 7/2014 | Domke et al. |
| 2014/0207874 A1 | 7/2014 | Soorianarayanan et al. |
| 2014/0207875 A1 | 7/2014 | Messinger et al. |
| 2014/0208159 A1 | 7/2014 | Soorianarayanan et al. |
| 2014/0208163 A1 | 7/2014 | Domke et al. |
| 2014/0244453 A1 | 8/2014 | Rephlo |
| 2015/0073832 A1 | 3/2015 | Goodnow et al. |

FOREIGN PATENT DOCUMENTS

| | | |
|---|---|---|
| CN | 1674030 A | 9/2005 |
| CN | 101982006 A | 2/2011 |
| EP | 1470781 A2 | 10/2004 |
| EP | 2465421 A1 | 6/2012 |
| GB | 2435113 A | 8/2007 |
| JP | 08-240589 A | 9/1996 |
| KR | 2003-0063426 | 7/2003 |
| KR | 2005-0072937 | 7/2005 |
| KR | 2005-0075502 A | 7/2005 |
| KR | 2008-0017470 A | 2/2008 |
| WO | WO2002/069793 A2 | 9/2002 |
| WO | WO2015/184462 A1 | 12/2015 |

OTHER PUBLICATIONS

World Health Organization; WHO guidelines on drawing blood; © 2010; 5 pages; retrieved from the internet (http://www.ncbi.nlm.nih.gov/books/NBK138671) on Aug. 14, 2015.

Armstrong; Blood Collection; ISBT Science Series; 3(2); pp. 123-136; Jun. 2008.

McDonald et al.; A novel rapid and effective donor arm disinfection method; Transfusion; 50(1); pp. 53-58; Jan. 2010.

Patel et al.; Impact of donor arm cleaning with different aseptic solutions for prevention of contamination in blood bags; Indian Journal of Hematol Blood Transfus; 29(1); pp. 17-20; Mar. 2013.

Kappestin; Nasokomiale Infektionen Pravention; Labordiagnostik; Antimkrobielle Therapie Thieme; 4th Edition; Jul. 15, 2009 (English Abstract).

Trautmann et al.; Anforderungen an die Hygiene bei Punktionen und Injektionen. Bundesgesundheitsblatt; Gesundheitsforschung; Gesundheitsschutz; vol. 54; pp. 1135-1144; Sep. 2011 (English Abstract).

\* cited by examiner

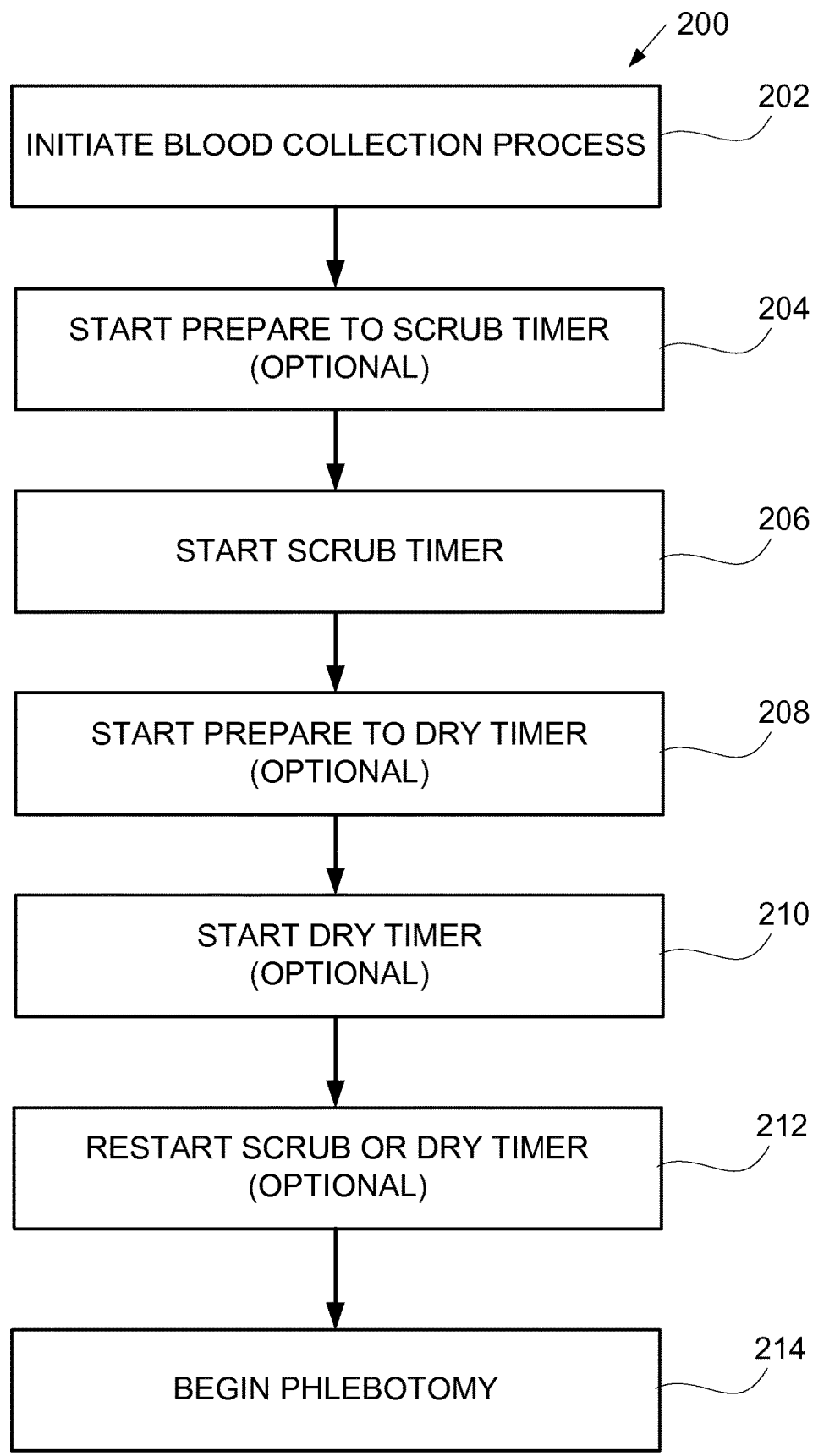

SYSTEMS AND METHODS FOR MANAGING BLOOD DONATIONS

CROSS REFERENCE TO RELATED APPLICATIONS

This application claims the benefit under 35 U.S.C. 119 of U.S. Provisional Patent Application No. 62/005,673, filed May 30, 2014, titled "SYSTEMS AND METHODS FOR MANAGING BLOOD DONATIONS". This application is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

Described herein are devices and methods for use in blood donation and blood management. In particular, described herein are devices and methods for acquiring blood donations.

BACKGROUND

Blood collection from a donor typically requires piercing the subject's skin with a needle, usually after the area of the subject's skin to be pierced is cleaned (e.g., with alcohol, iodine, or the like). Bacteria present on the skin can enter the blood component collecting bag together with the blood. Indeed, it has been found that some kinds of skin-borne bacteria that may enter the blood collecting bag in this manner may multiply even if blood collecting bag is kept cold. When the collected blood is transfused into a patient, the patient may suffer from infectious disease or blood poisoning.

Although most phlebotomists are trained in techniques to wash or prepare the skin prior to collecting blood, there is a great deal of variability and simple human error associated with collection of blood. For example, the time required to adequately prepare the skin site for needle penetration, including both washing and drying the skin, is not standardized. Even where standard times are applied for each of these steps (e.g., 30 second scrub time), the phlebotomist is generally expected to time herself or himself. Thus, there is a potential for further error and variability which may result in contamination of the collected blood.

The current technique used by most phlebotomists allows the phlebotomist to use a time piece to time a scrubbing procedure, generally their own watch or a clock on the wall. In many instances, a phlebotomist may use one time piece, such as their watch, to initiate a scrubbing procedure, and may then use another time piece, such as a clock on the wall, to monitor the end of the scrubbing procedure. Non-compliance with standardized scrub times can result when the time is not synchronized between these two time pieces. When non-compliance is observed by the FDA, the blood center can be given a 483 non-compliance write-up and be required to respond with a Corrective and Preventative Action, which costs the blood center both time and money.

In view of this and other problems, there is a need for tools, including blood collection apparatuses that may help address these issues. In particular, described herein are blood collection devices that are adapted to provide multiple easy-to-use and accurate timers that may guide the phlebotomist in preparing the subject's skin, and can prevent collection from improperly cleaned skin, as well as methods of using such devices.

SUMMARY OF THE DISCLOSURE

In general, described herein are apparatuses and methods of using them to collect blood by first ensuring that the patient's skin is properly cleaned, to prevent contamination of the collected blood. Any of the devices described herein may include an integrated controller with a timer having multiple modes to guide a user (e.g., a phlebotomist) in prepping a subject's skin for a blood draw. The system may include a display (visual) and/or audible output to guide the user, such as a pre-configured countdown for a timer that establishes a predetermined cleaning and drying time (and also potentially additional cleaning/drying cycles). The timer may be hands-free, so that the user only has to trigger the first activation, additional time cycles may be triggered automatically. The system may include a controller that also interfaces with the timer and may record compliance. The system may include a restart function, allowing the user to restart the pre-configured countdown if the cleaning and drying time is missed for any reason. Additionally, the system may include an automated restart function, wherein the pre-configured countdown is restarted if a user reaches the end of the cleaning and drying time without proceeding to the blood collection process for longer than a configured time period.

For example, a blood collection apparatus may include a countdown beep during a preparing to clean (prepare to scrub) period and/or a prepare to dry time period, and/or during a drying period and/or during a cleaning period. In some variations the apparatus or method of operating the apparatus includes a countdown beep only during the preparing time periods (e.g., preparing to clean and preparing to dry time periods). During any of these time periods (first preparing to clean time period, first cleaning time period, second preparing to clean time period, second cleaning time period, preparing to dry time period, drying time periods) a visual countdown may be shown on the display, with or without an audible count down. For example, in some variations a visual countdown may be shown on the display only during the scrub and dry time periods (including displaying without an audible countdown). At the beginning and end of any of these time periods (e.g., the scrub and dry periods), a distinctive audible tone may be made to signal the start or end of that period so the phlebotomist need not be watching the display.

For example, described herein are methods of collecting blood from a patient, the method comprising: initiating, in a blood collection device, a scrub timer having a scrub time period; during the scrub time period, disinfecting tissue of the patient at a needle entry site; and after the scrub time period has elapsed, beginning a blood draw process. The method may include emitting one or more audible beeps from the collection device at the start of the scrub period. The method may include emitting one or more audible beeps from the collection device during the scrub period. The tones emitted may be different. For example, the tones emitted at the start of a preparing to dry period, dry period, preparing to clean period, cleaning period, etc. may be different from each other and from the tones emitted to count down these periods. For example, the tones may be different in frequency, pitch, volume, scale, intensity, etc. Thus, for example, the method may include audibly counting down the scrub time period. For example, the method may include emitting a series of audible beeps counting down the scrub period. In some variations, the method may include: initiating, in the blood collection device immediately after the scrub time period has elapsed, a prepare to dry timer having a prepare to dry time period; and audibly counting down the prepare to dry period. The method may also include initiating, in the blood collection device immediately after the scrub time period has elapsed, a prepare to dry timer having a prepare to dry time period; during the prepare to dry period, performing a secondary wash of the patient at the needle entry site; and audibly counting down the prepare to dry period during the prepare to dry time period. After the disinfecting tissue step, the method (system) may automatically initiate in the blood collection device a dry timer having a dry time period; and drying tissue of the patient at the needle entry site during the dry time period.

For example, described herein are methods of collecting blood from a patient, the method comprising: initiating, in a blood collection device, a scrub timer having a scrub time period; audibly counting down the scrub timer during the scrub time period; automatically initiating, in the blood collection device after the scrub time period has elapsed, a dry timer having a dry time period; audibly counting down the dry timer during the dry time period; and beginning a blood draw process after the dry time period has elapsed. The method may also include initiating, in the blood collection device immediately after the scrub time period has elapsed, a prepare to dry timer having a prepare to dry time period; and audibly counting down the prepare to dry period.

Devices and systems configured to implement these methods are also included. For example, a blood collection device may include: a support configured to hold a blood collection bag; a pinch valve configured to engage a tube leading from the blood collection bag to a patient; a controller configured to control the blood collection device including the pinch valve; and a scrub timer coupled to the controller and configured to indicate to a user a scrub time period prior to beginning a blood draw process.

BRIEF DESCRIPTION OF THE DRAWINGS

FIG. 2 is a flowchart describing an integrated scrub timer in a blood collection device.

DETAILED DESCRIPTION OF THE DISCLOSURE

Figure 1:
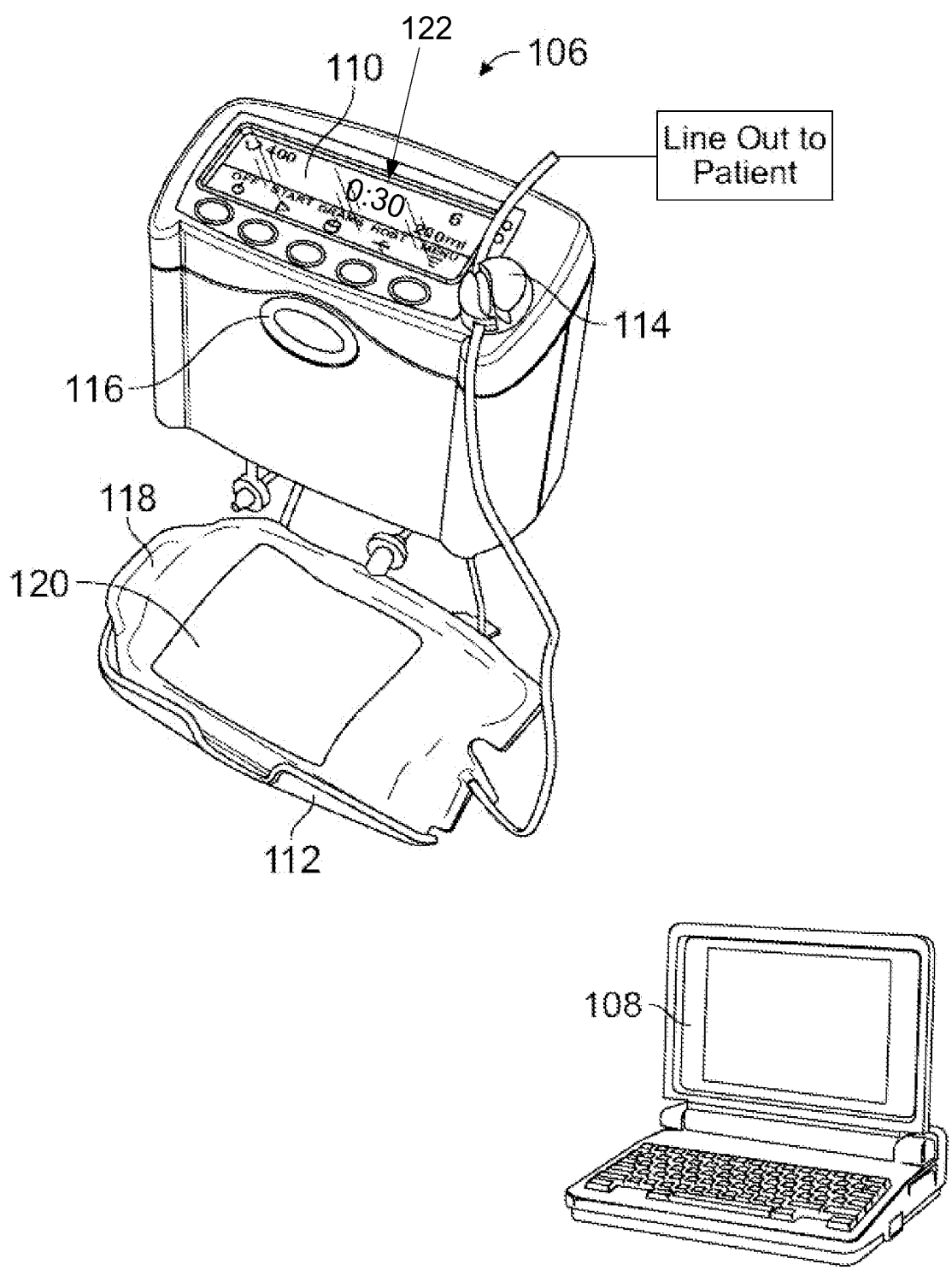
FIG. 1 is an illustration of a blood collection device and a control system.

FIG. 1 is a diagram showing a blood collection device 106 and optional control system 108. In some embodiments, the blood collection device 106 is a standalone device and does not use or interact with a control system 108. In other embodiments, more than one blood collection device 106 can be networked with and bi-directionally communicate with the control system 108. Blood collection device 106 can provide blood banks and other blood collection centers with an inexpensive yet accurate device for managing and monitoring the collection of blood donations from blood donors. The device is configured to accurately weigh blood donations during the collection process, and to provide blood bag mixing to insure correct disbursement of anticoagulant and alleviate the need for manual mixing by a phlebotomist. Referring to FIG. 1, blood collection device 106 can include a graphical user interface (GUI) 110, a scale or bag tray 112, a pinch valve 114, and a barcode scanner 116. The device can be configured to receive a blood donation bag 118 on the scale and in the pinch valve, as shown. In some embodiments, the blood donation bag comprises a barcode 120 readable via the barcode scanner of the blood collection device.

The GUI 110 allows a user (e.g., a phlebotomist) to configure, calibrate, and setup the blood collection device for use. GUI 110 may display information to the user such as calibration status of the blood collection device 106. In some embodiments, the GUI 110 displays information to the user such as calibration status of the device bag tray 112, weight of the blood donation bag 118, and operation status of the device (e.g., calibration, blood collection underway, blood collection complete, errors during collection, etc.). During initial setup of the device, a user may be asked to zero or calibrate the device, with no weight on the bag tray 112 to ensure accurate measurement of collected blood.

In some embodiments, the device comprises an agitation system suspended on the internal load cell. The agitation system can comprise a motor-driven crank configured to agitate/shake the bag tray 112 and the blood donation bag 118 during blood collection. The agitation system can be designed for minimal weight and optimized for the power required to agitate/shake the bag tray 112 and thus, the blood bag.

When a blood collection bag is placed on the bag tray 112, vertical oscillations of the agitation system can cause blood collected from a donor to flow from one end of the bag to the other, resulting in gentle mixing of the blood and the contained anticoagulant and/or additives. Since the agitation system is mounted on the internal load cell, the load cell can then sense the weight of the bag tray 112, the agitation system, the blood bag, and the accumulated blood.

The blood collection device can further include a pinch valve 114 configured to open and close the blood bag line leading from the patient to the blood donation bag 118. Thus, the blood collection device can be configured to open the pinch valve 114 when the blood collection process begins and close the pinch valve when the blood collection is complete, e.g., when the load cell indicates that the blood donation bag is full.

The blood collection device is configured to automatically measure the weight of accumulated blood during the blood collection process. In some embodiments, the weight of the accumulated blood is measured every time the blood bag and bag tray 112 are in a relatively stable position. In other embodiments, the accumulated blood is measured continuously. By regularly monitoring the weight of collected blood, the blood collection device can calculate blood flow rates from the patient to the blood collection bag. The weight measurements and or flow rates can be used to determine when the blood collection process is complete.

When a blood collection is started, the blood collection device can first implement a series of weight readings of the empty blood bag, the agitation system, and the bag tray assembly. This can be recorded in the device's memory as the tare weight. The desired collection volume can be converted mathematically from weight to volume by using the specific gravity of blood, e.g., of 1.058. (1.00 ml of blood weighs 1.058 grams); this may be configurable on the device between 1.050 to 1.060. This converted weight value plus the tare weight results in the target weight and is compared against on-going weight readings as the collection proceeds. The blood collection device can then open the pinch valve to begin the blood collection process.

The agitation system can be left off until a small increase in weight is seen over the tare weight. As soon as the weight increase is seen by the blood collection device, the agitation system can initiate the shacking/rocking, and various other timing and flow functions can be activated. The blood collection device can continue to read the weight of the blood collection bag. Although these readings are relatively accurate, in some embodiments for greater accuracy, the blood collection system can stop the agitation process when the total weight is slightly less than the target weight. The final readings of collected blood can then be taken with the bag and bag tray in a horizontal position. At this point, it is unnecessary to continue agitating the bag since the anticoagulant is already fully mixed with the blood in the bag. Alternatively, the shaking/rocking could continue throughout the collection provided that accuracy of the weight readings could be assured.

Typically blood bank standards require that blood collections must be completed in a set period of time (20 minutes maximum for current US regulations), smaller volumes of collection can tolerate a slower flow rate. In some embodiments, the blood collection device measures the flow rate and compares it against a computed constant, equal to a minimum flow value for the set period of time described above. As a result, if the required volume is greater, the flow rate must be greater to accomplish the fill in the set period of time (e.g., 20 minutes). If the required volume is less, the flow rate can be slower.

The blood collection device 106 can also include a barcode scanner 116 configured to read a barcode as an input to the device. For example, donation ID's unique to individual donors can be scanned during the blood collection process to keep track of all collection events related to that unique donation ID. In one embodiment, the donation ID can be represented as a barcode 120 located on blood donation bag 118.

The blood collection device 106 can be in communication with control system 108 during all steps of the blood collection process described above (e.g., calibration, blood collection, scrub and dry timing, and completion of the blood draw). The blood collection device and control system can communicate via any technology known in the art, such as wirelessly through a WiFi or Bluetooth connection, or through a wired Ethernet connection. The control system can comprise a computer having all the necessary hardware (e.g., CPU, memory, data storage, etc.) required to execute a data collection and management software.

Scrub Timer

In some embodiments, the blood collection device 106 can include a scrub timer 122. The scrub timer can be configured to aid a phlebotomist in cleaning and preparing a needle entry site prior to blood collection. Some blood collection requirements or guidelines require that a needle entry site of the patient be scrubbed or cleaned for a certain period of time. For example, prepping for a blood collection typically involves disinfecting the tissue around the needle entry site for at least 30 seconds with a 70% or higher alcohol swab, or alternatively, with an iodine solution. The tissue can then be dried before the blood collection process begins. If this disinfecting step is skipped, or if the phlebotomist does not scrub the tissue entry site for the proper amount of time, the blood collected from that patient can be compromised.

Referring still to FIG. 1, a scrub timer 122 can be implemented in the blood collection device 106. The scrub timer 122 can be a visual timer displayed on the GUI 110 (e.g., in the form of a countdown or other visual indicator), or alternatively can be an audible timer that is conveyed to the user or phlebotomist with spoken words, beeping, or other sounds. In some embodiments, the duration of the scrub timer can be pre-set by a user or the phlebotomist, depending on the desired scrub time. In other embodiments, the scrub timer can include both a first timer that tracks the scrubbing or disinfecting process, and second timer that tracks drying of the tissue around the needle entry site after the scrub, or a second scrub. The scrub timer 122 can optionally include a countdown timer before or after each of the first and second timers, to give a user or phlebotomist time to prepare for impending action. The scrub timer 122 can optionally include a manual and/or automated restart function, in which the scrub and/or dry timer is restarted in the blood collection device due to non-compliance. For example, a phlebotomist can manually restart the scrub and/or dry timer if the needle entry site was not prepared properly during the scrub time period, or alternatively, the blood collection device can automatically restart the scrub and/or dry timer if the blood collection process isn't started within a pre-determined period following completion of the scrub and/or dry timer.

FIG. 2 is a flowchart 200 describing the use of the scrub timer described above. All references to a blood collection device or scrub timer in this section can refer to blood collection device 106 and scrub timer 122 of FIG. 1. At step 202 of flowchart 200, a user of a blood collection device, such as phlebotomist, can initiate a blood collection process on the blood collection device. The user can, for example, turn on the blood collection device and push a button on the device to start the process.

Next, at step 204 of flowchart 200, the blood collection device can optionally start a "prepare to scrub" timer. This "prepare to scrub" timer can be displayed or audibly presented to the user to prepare them for the next step. For example, the "prepare to scrub" timer can be a short countdown, e.g., 5 seconds, to indicate to the user of the blood collection device that the scrub step is about to begin. In some embodiments, there is no "prepare to scrub" timer and the blood collection device goes directly from step 202 to step 206, below.

At step 206 of flowchart 200, the blood collection device can start the scrub timer. As described above, the duration of the scrub timer can be pre-set by the user, and can be a visual countdown or timer, or optionally can be audible words, beeps, or sounds. If the scrub timer is a visual countdown or running timer displayed on a GUI of the blood collection device, the user can look at the device to see how much time remains or has passed in the scrub. When the scrub timer begins in step 206, the user or phlebotomist can begin scrubbing the patient's skin surrounding the needle entry site, and can stop the scrubbing process when the scrub timer expires (or reaches the pre-configured scrub time). Scrubbing during the entire duration of the scrub timer ensures that proper scrub protocol has been followed by the phlebotomist.

In some scenarios, a phlebotomist may be required to perform a secondary scrub, or alternatively, may be required to dry the tissue around the needle entry site after the initial scrub. For example, some alcohol based scrubs require that the skin be dried before a needle is inserted into the patient. Alternatively, if an iodine solution is used for the initial scrub, some blood centers require a secondary scrub to further disinfect the patient. In either of these instances, steps 208 and 210 can be optionally implemented with a scrub timer feature of a blood collection device during a blood collection process.

At step 208 of flowchart 200, the blood collection device can optionally start a "prepare to dry" timer. This "prepare to dry" timer can be displayed or audibly presented to the user to prepare them for the next step. For example, the "prepare to dry" timer can be a short countdown, e.g., 5 seconds, to indicate to the user of the blood collection device that the drying step is about to begin. In some embodiments, the "prepare to dry" timer can be replaced with a second "prepare to scrub" timer if a second scrub is required.

At step 210 of flowchart 200, the blood collection device can start the dry timer. As described above, the duration of the dry timer can be pre-set by the user, and can be a visual countdown or timer, or optionally can be audible words, beeps, or sounds. If the dry timer is a visual countdown or running timer displayed on a GUI of the blood collection device, the user can look at the device to see how much time remains or has passed in the drying process. When the dry timer starts in step 210, the user can begin the drying process, and can stop the drying process when the dry timer expires (or reaches the pre-configured dry time). As with step 208, the dry timer can be replaced with an optional second scrub timer if a second scrub is required.

At step 212 of flowchart 200, the scrub and/or dry timer can manually or automatically be restarted. For example, if the phlebotomist fails to comply with the scrub and/or dry timer and realizes the non-compliance, the phlebotomist can interface with the blood collection device to restart the scrub and/or dry timer (e.g., by pushing a button on the device). Alternatively, the blood collection device can automatically restart the scrub and/or dry timer if for example, the phlebotomy process does not begin within a predetermined time period following the completion of the scrub and/or dry time period.

Finally, at step 214 of flowchart 200, the phlebotomy process can begin, and blood can be drawn from the patient. Steps 202-212 above can be implemented in a scrub timer of the blood collection device to ensure that proper scrub protocol is followed, thereby decreasing the chances that the blood collected from the patient is rejected for failing to follow scrub protocol.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of collecting blood from a patient, the method comprising:
   initiating, in a blood collection device, a scrub timer having a scrub time period;
   during the scrub time period, disinfecting skin tissue of the patient at a needle entry site with a disinfectant; and
   after the scrub time period has elapsed, beginning a blood draw process with the blood collection device.

2. The method of claim 1, further comprising emitting one or more audible beeps from an audible output of the collection device during the scrub period.

3. The method of claim 1, further comprising emitting one or more audible beeps from an audible output of the collection device to indicate the start of the scrub period.

4. The method of claim 1, further comprising audibly counting down the scrub time period with an audible output of the collection device.

5. The method of claim 1, further comprising visibly counting down the scrub time period with a graphical user interface of the collection device.

6. The method of claim 1, further comprising emitting a series of audible beeps counting down the scrub period with an audible output of the collection device.

7. The method of claim 1, further comprising: initiating, in the blood collection device immediately after the scrub time period has elapsed, a prepare to dry timer having a prepare to dry time period; and counting down the prepare to dry period.

8. The method of claim 7, further comprising emitting one or more audible beeps from an audible output of the collection device to indicate a start of the prepare to dry time period.

9. The method of claim 7, further comprising audibly counting down the prepare to dry time period with an audible output of the collection device.

10. The method of claim 7, further comprising emitting one or more audible beeps counting down the prepare to dry time period with an audible output of the collection device.

11. The method of claim 7, further comprising visibly counting down the prepare to dry time period with a graphical user interface of the collection device.

12. The method of claim 1, further comprising: initiating, in the blood collection device immediately after the scrub time period has elapsed, a prepare to dry timer having a prepare to dry time period; during the prepare to dry period, performing a secondary wash of the skin tissue of the patient at the needle entry site; and counting down the prepare to dry period.

13. The method of claim 1, further comprising: after the disinfecting tissue step, automatically initiating in the blood collection device a dry timer having a dry time period; and drying skin tissue of the patient at the needle entry site during the dry time period.

14. The method of claim 1, further comprising emitting one or more audible beeps from an audible output of the collection device during the scrub period.

15. The method of claim 1, further comprising emitting one or more audible beeps from an audible output of the collection device to indicate a start of the scrub period.

16. The method of claim 1, further comprising audibly counting down the scrub time period with an audible output of the collection device.

17. The method of claim 1, further comprising visibly counting down the scrub time period with a graphical user interface of the collection device.

18. The method of claim 1, further comprising emitting a series of audible beeps counting down the scrub period with an audible output of the collection device.

19. The method of claim 1, further comprising; before the scrub time period, initiating, in a blood collection device, a prepare to scrub timer having a prepare to scrub time period; and counting down the prepare to scrub time.

20. The method of claim 1, further comprising automatically restarting the scrub timer if the blood draw process does not begin within a pre-determined time period following the scrub time period.

21. A method of collecting blood from a patient, the method comprising:
   initiating, in a blood collection device, a scrub timer having a scrub time period;
   visibly and/or audibly counting down the scrub timer during the scrub time period with a graphical user interface and/or an audible output of the blood collection device;
   automatically initiating, in the blood collection device after the scrub time period has elapsed, a dry timer having a dry time period;
   visibly and/or audibly counting down the dry timer during the dry time period with the graphical user interface and/or the audible output of the blood collection device; and
   beginning a blood draw process with the blood collection device after the dry time period has elapsed.

22. The method of claim 21, further comprising initiating, in the blood collection device immediately before the scrub time period, a prepare to scrub period; and visibly or audibly counting down the prepare to scrub period with the graphical user interface or the audible output of the blood collection device.

23. The method of claim 21, further comprising emitting one or more audible beeps from an audible output of the blood collection device before initiating the dry time period.

24. The method of claim 21, further comprising emitting one or more audible beeps from an audible output of the blood collection device before initiating the scrub time period.

25. The method of claim 21, further comprising initiating, in the blood collection device immediately after the scrub time period has elapsed, a prepare to dry timer having a prepare to dry time period; and visibly or audibly counting down the prepare to dry period with the graphical user interface or the audible output of the blood collection device.

26. The method of claim 1 wherein the disinfectant comprises an alcohol solution.

27. The method of claim 1 wherein the disinfectant comprises an iodine solution.

\* \* \* \* \*